United States Patent [19]

Stjernholm

[11] E Patent Number: Re. 33,071

[45] Reissued Date of Patent: Sep. 26, 1989

[54] PLATINUM BOUND TO TRANSFERRIN FOR USE IN THE TREATMENT OF BREAST TUMORS

[76] Inventor: Rune L. Stjernholm, c/o Department of Biochemistry, Tulane Medical School, 1430 Tulane Ave., New Orleans, La. 70112

[21] Appl. No.: 140,659

[22] Filed: Jan. 4, 1988

Related U.S. Patent Documents

Reissue of:

[64] Patent No.: 4,590,001
Issued: May 20, 1986
Appl. No.: 593,725
Filed: Mar. 27, 1984

U.S. Applications:

[63] Continuation-in-part of Ser. No. 479,173, Mar. 28, 1983, abandoned.

[51] Int. Cl.[4] ..... C07K 15/06; A61K 37/02; A61K 35/14; A61K 33/24

[52] U.S. Cl. ..... 530/394; 530/402; 424/101; 424/649; 514/6

[58] Field of Search ..... 514/6; 424/101, 131; 530/402, 394

[56] References Cited

PUBLICATIONS

Stjernholm et al, Bioinorganic Chem. 9, pp. 277–280 (1978).

Bodanszky et al, in *The Peptides,* vol. 5 (1983) p. 156.

Aisen et al, J. Biol. Chem. 244, No. 17 (1969) pp. 4628–4633.

Rosenberg et al, J. Biol. Chem. 242, No. 6 (1967) pp. 1347–1352.

Gullo et al, Cancer Chemother. Pharmacol., 5, (1980), pp. 21–26.

Stjernholm et al, "The Binding of Platinum to Human Transferrin", Bioinorganic Chem., 9, 277–280 (1978).

Bodansky et al, "Side Reactions in . . . ", in *The Peptides,* vol. 5, Gross et al. eds, 1983, p. 156.

Aisin et al., "The Chronium, Magnesium and Cobalt Complexes of Transferrin", J. Biol. Chem., 244, No. 17, pp. 4628–4633.

*Primary Examiner*—Johnnie R. Brown
*Assistant Examiner*—Jacqueline M. Stone
*Attorney, Agent, or Firm*—Klarquist, Sparkman, Campbell, Leigh & Whinston

[57] ABSTRACT

A method of preparing an anti-breast tumor compound comprised of a toxic metal bound to the blood protein transferrin is disclosed which has superior therapeutic properties. When monomeric transferrin is bound to cis-Dichlorodiammineplatinum (II), a chemotherapeutic agent is produced which specifically attacks and kills rapidly multiplying breast tumor cells without damaging normal cells. In addition, the body's immune defenses against foreign substances are substantially not activated. In preferred embodiments, 1.8–2.2 atoms of platinum are bound to each molecule of transferrin. The platinum-transferrin is prepared by first protecting the sulfhydro groups on essentially iron free transferrin with an excess of cystine in solution. Cis-dichlorodiamine platinum (II) is then reacted with the iron-free transferrin in the presence of bicarbonate anion. The platinum transferrin is dialyzed to remove the weak organic acid and bicarbonate anion, and then passed through molecular sieves to separate the monomeric product which is thereafter concentrated to a therapeutically useful concentration.

5 Claims, 2 Drawing Sheets

PLATINUM BOUND TO TRANSFERRIN FOR USE IN THE TREATMENT OF BREAST TUMORS

Matter enclosed in heavy brackets [ ] appears in the original patent but forms no part of this reissue specification; matter printed in italics indicates the additions made by reissue.

CROSS REFERENCE TO RELATED APPLICATION

This application is a continuation-in-part of U.S. patent application Ser. No. 479,173 Mar. 28, 1983, now abandoned.

BACKGROUND OF THE INVENTION

Transferrin is a protein found in the blood of all humans and its known function is to carry iron to those organs and cells of the body that require this metal for normal function. Recently, scientists have reported that an important function of iron carried by transferrin is to control the division of body cells. E. Robbins et al. Proceedings National Acadeny Science U.S.A., 66: 1244 (1970); P. Rudland, et al., Biochemical Biophysical Research Communications, 75: 556 (1977). It has been known for some time that when a person becomes afflicted with a neoplastic growth, the quantity of iron in the blod carried by transferrin is severely diminished. M. Beamish, et al., British Journal of Cancer, 26: 444 (1972); N. Hughes, Australian Journal of Experimental Biological Medicine Science, 50: 97 (1972). The applicant of the present invention and others investigated this depletion of iron bound to transferrin in the blood of rats with malignant tumors, and found that the iron had not left the body, but instead had been relocated and accumulated in tissue containing neoplastic cells. F. Warner, R. Stjerhnolm, and I. Cohn, Medical Physics, 5: 100 (1978); N. Dodd et al., British Journal of Cancer, 34: 556 (1976). It was also observed that when the rat tumor was put into remission by a variety of anti-neoplastic drugs, the serum levels of transferrin bound iron returned to normal. These results indicated that when the tumor cells are not multiplying, iron was not concentrated in the neoplasms. F. Warner, M. de Manuelle, R. Stjernholm, I. Cohn and W. Baddley, Journal of Clinical Hemotology and Oncology, 7: 180 (1977). Other research leading to the instant patent showed that human breast carcinoma tissue contained larger quantities of transferrin bound iron than surrounding apparently normal tissue. F. Santoliguido, et al. Surgery, Gynecology and Obstretics, 142: 65 (1976); W. Faulk, Lancet, pg. 390, Aug. 23, 1980. For iron specifically bound to transferrin to play such a vital role in controlling cell division, the intracellular chemistry of cell division must be so unique that if natural transferrin bound iron is properly replaced by another metal, disruption of the cell division processes will occur.

Since platinum was already known to kill cancer cells, J. Marks, Science, 192: 774 (1976), Cancer Treatment Chemotherapy (C. Haskell, ed.) W. B. Saunders Co., pgs. 112–114 (1980); "Proceedings Third International Symposium on Platinum Coordination Complexes in Cancer Chemotherapy", Journal Clinical Hemotology & Oncology, Vols. 1 and 2 (1977), the applicant chose it as a metal to replace iron on the protein transferrin. R. Stjernholm, et al., Bioinorganic Chemistry, 9: 277 (1978). Because of its toxicity, platinum has been used in the past in organometallic moieties and compounds to treat neoplastic growths, for instance in the U.S. Pat. Nos. 4,053,587, 4,151,185, 4,169,846, 4,175,133, 4,177,263, 4,206,208, 4,234,499, 4,234,500, 4,284,579. However, these previous therapeutic agents incorporating platinum had severe drawbacks in a clinical context. Specifically, the platinum chemotherapeutic agents would not specifically attack and kill the neoplastic cells, but instead caused damage to normal cells as well. Many of the platinum compounds also activated the body's immune systems, creating further side effects and causing the foreign substances to be rapidly removed from the body, thereby reducing the therapeutic effect of the drugs. These platinum based chemotherapeutic agents can cause kidney dysfunction, hearing problems, and intestinal antagonism. J. Marks, Science, 192: 774 (1976), Cancer Treatment Chemotherapy (Haskell, ed.), W. B. Saunders Co., pgs 112–114 (1980). "Proceedings Third International Symposium on Platinum Coordination Complexes in Cancer Chemotherapy", Journal of Clinical Hematology & Oncology, Vols. 1 and 2 (1977). Under certain circumstances, kidney failure results, which in itself can be fatal. Even most of the non-metal based cancer treatments cause traumatic side effects: falling out of hair, nausea, etc.

The specific form of the platinum starting material which has been found most useful in therapeutic applications is cis-Dichlorodiammineplatinum (II). The invention is not limited to cis-Dichlorodiammineplatinum (II), since other inorganic platinum starting materials may be useful. However, most research to date in the field of oncology has focused on cis-Dichloradiammineplatinum (II) (cis-platinum)

SUMMARY OF THE INVENTION

In accordance with the present invention, a novel treatment for breast cancer has been devised having properties which give it the potential for treating breast cancer. The unique characteristics of this new anti-neoplastic chemotherapeutic agent that make it so attractive are (1) its potential capability of specifically killing breast tumor cells while having little or no effect on normal, slower growing cells; (2) it is relatively inexpensive to manufacture, thereby making it more generally available to cancer victims; (3) it is not recognized as a foreign substance by the body's immune system since the platinum is cloaked in a naturally occuring body protein.

Platinum-transferrin is prepared by reacting at 0°–5° C. cis-platinum dichlorodiammine platinum (II), or other inorganic platinum compounds, with pure, essentially iron-free transferrin in the presence of bicarbonate anion after chemically protecting the sulfhydro groups of the transferrin with an excess of cystine. The platinum transferrin is dialyzed to remove the weak organic acid and bicarbonate anion, passed through molecular sieves to separate polymeric platinum-transferrin from the monomeric product, and the monomeric product is thereafter concentrated to a therapeutically useful concentration.

DETAILED DESCRIPTION OF THE INVENTION

Figure 1:
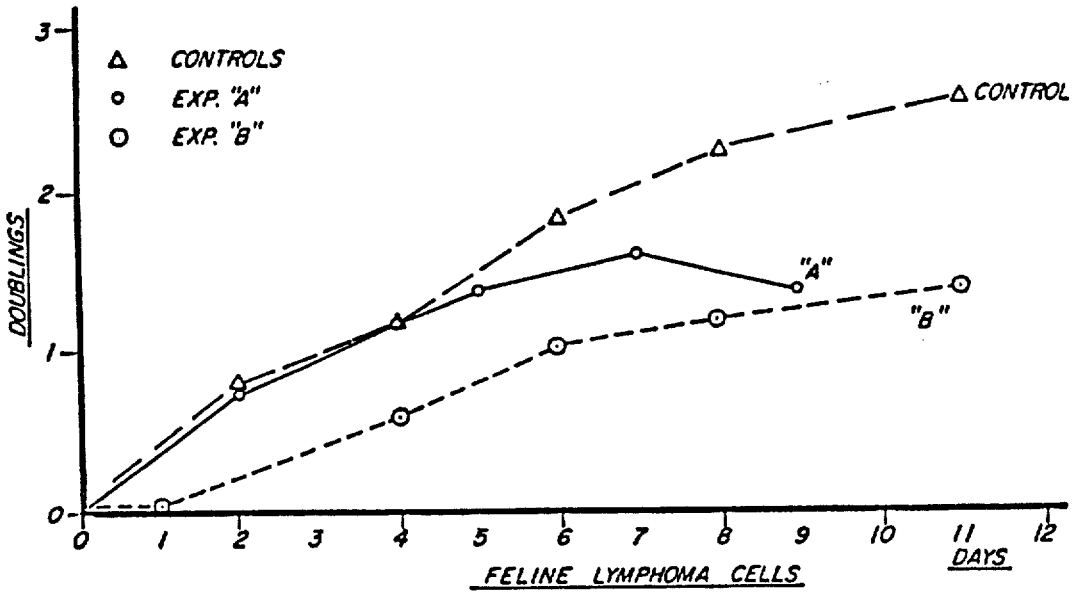

An active complex of platinum-transferrin prepared by reacting essentially iron free human transferrin with cis-diamminedichloroplatinum II has been devised and tested on several cell lines in culture. FIG. 1 shows that the rate of growth of feline lymphoma cells was slowed to approximately one-half that of the controls when treated with platinum-transferrin dissolved in phosphate buffered saline. The doubling time for the treated cells was 7.8 days as compared to 4.4 days for untreated control cells. Even though these feline cells were not killed the results are very important because human transferrin, which was used, is not generally genetically compatible with cat cells.

Figure 2:
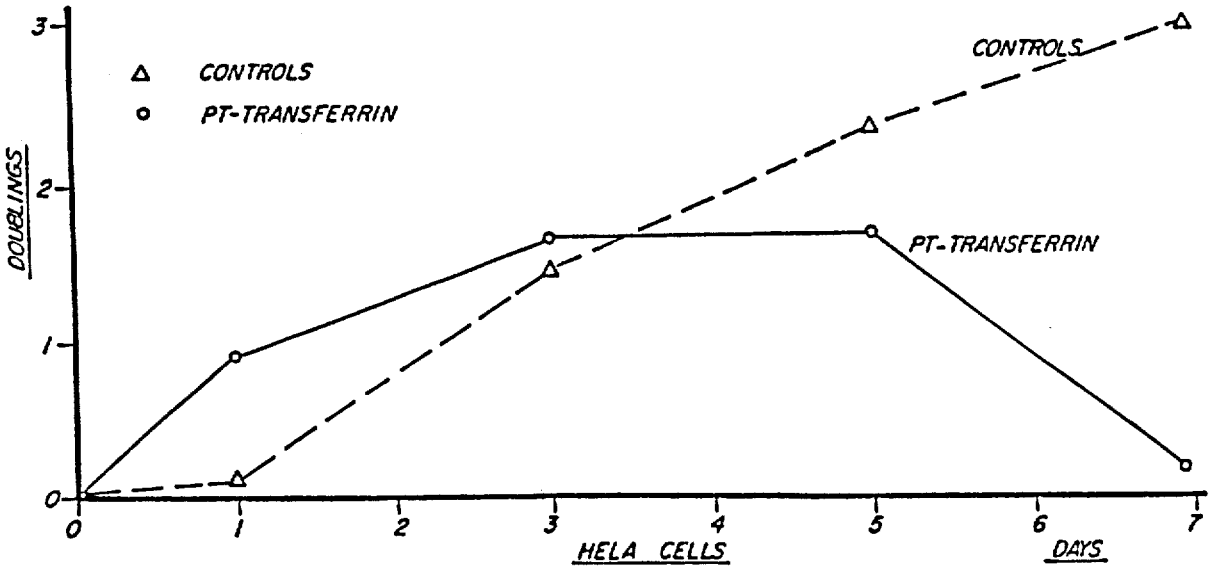

In FIG. 2, platinum-transferrin is shown to kill human HeLa cells (derived from human cervical cancer) within 7 days. It is interesting to note from FIG. 2 that the killing process was initiated immediately upon exposure to platinum-transferrin. (Platinum-transferrin was introduced into the culture medium 24 hours after seeding.)

Figure 3:
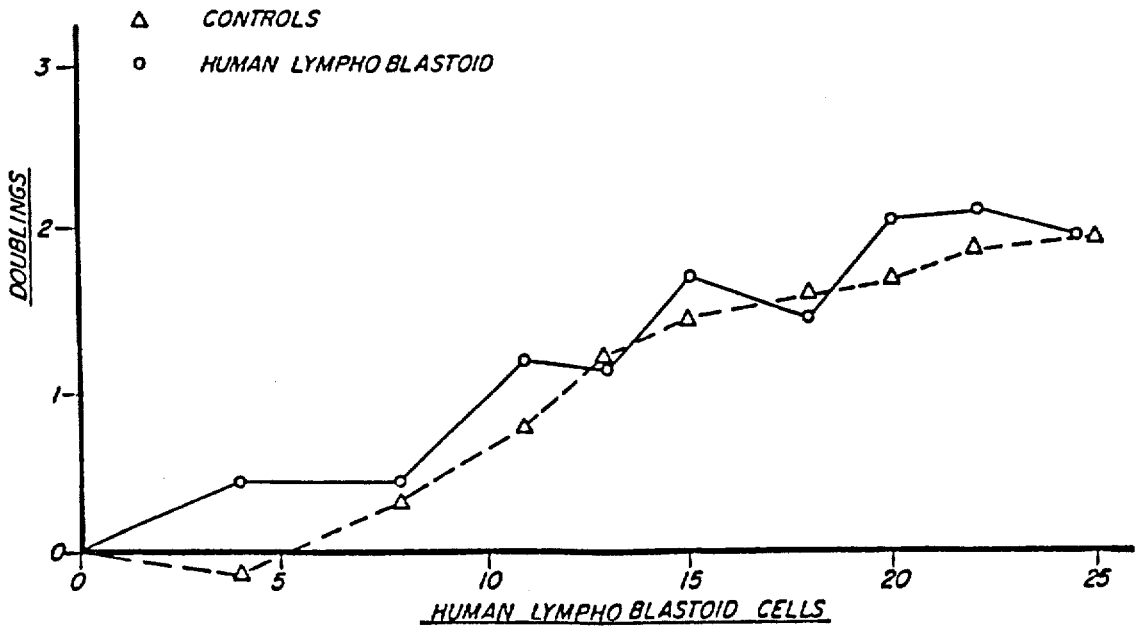
Figure 4:
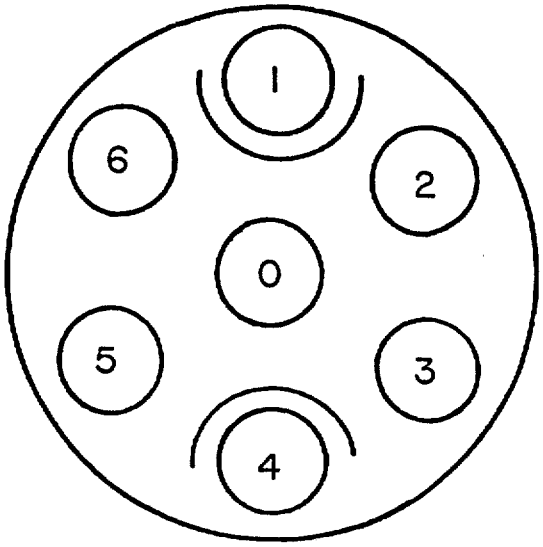

The effect of platinum-transferrin on a slow growing human cell line (lympho blastoid cells) is demonstrated in FIG. 3. In this case, in which the lympho blastoid cells simulated normal, non-malignant cells in the human body, no adverse effects were observed. Accordingly, it appears that the cis-platinum-transferrin composition specifically accumulates in the neoplastic cells without accumulating in or damaging normal, non-malignant cells.

This tissue cultures leading to the results shown in FIGS. 1–3 were prepared by obtaining the feline lymphoma cells, human HeLa tissue, and lympho-blastoid cell cultures from the American Type Culture Collection, which is the usual source of such materials. The cultures were placed in flasks in Eagle's medium, and the flasks were placed in a computerized incubator of the type that is well known in the art. The incubator was maintained at 37° C., which a humidity of about 70%, and the air contained about 5% $CO_2$. The tissue cultures were then checked every two days and the doublings counted to obtain the data shown in FIGS. 1–3. When a 10% excess of platinum-transferrin dissolved in phosphate buffered saline was pipeted into the culture medium, cell growth began to decrease.

Additional clinical data has been collected by administering platinum-transferrin prepared by applicant in accordance with the methods of preparation outlined in Examples I and II to seven human patients suffering from infiltrating lobular carcinoma of the breast, some having metastatic complications. Three of the seven patients to whom platinum-transferrin was administered were already moribund at the time of first injection, and because of their extensive underlying physical deterioration, they died in spite of the treatment. The other four patients who have received the drug, however, have all improved dramatically, showing signs of remission or disappearance of disease.

Patient A was a 38-year-old white female suffering from infiltrating lobular carcinoma who had undergone a total mastectomy and axillary dissection. She was later found to have leptomeningeal metastasis with spinal fluid showing viable tumor cells; there was also evidence of bone involvment. After a conventional course of chemotherapy on Nolvadex and Methotrexate had failed, the patient's condition continued to worsen until she became practically moribund. Therefore, she was started on a course of platinum-transferrin intravenously, and improved dramatically. She was given injections in the following amounts during the indicated weeks, wherein week 1 was the week during which the initial dose was administered:

| | |
|---|---|
| Week 1 | 810 mg. |
| Week 2 | 257.3 |
| Week 3 | 184.5 |
| Week 7 | 724.45 |
| Week 8 | 939.35 |
| Week 18 | 207 |
| Week 21 | 317 |
| Week 23 | 397 |
| Week 24 | 314 |
| Week 28 | 354 |
| Week 29 | 340 |
| Week 30 | 304 |
| Week 35 | 324 |
| TOTAL | 5472.60 mg. |

After this course of therapy the patient was evaluated and had no apparent evidence of leptomeningeal metastasis or other marked systemic diease.

Patient B was a 52-year-old white female with far advanced local carcinoma of the left breast who was diagnosed as having a very aggressive infiltrating ductal carcinoma. After traditional chemotherapy with Tamoxifen (Nolvadex) showed little response, she was started on the platinum-transferrin complex and given injections regularly. These injections were given on the following dates in the indicated amounts:

| | | |
|---|---|---|
| Patient B | Week 1 | 1278 mg |
| | Week 3 | 1191 |
| | Week 3 | 1002 |
| | Week 5 | 1196 |
| | Week 7 | 1198 |
| | Week 8 | 1130 |
| | Week 11 | 1195 |
| | Week 13 | 1130 |
| | Week 15 | 1400 |
| | Week 16 | 1334 |
| | Week 18 | 1102 |
| | Week 21 | 1379 |
| | Week 24 | 841 |
| | Week 29 | 689 |
| | Week 32 | 1106 |
| | Week 35 | 982 |
| | Week 39 | 946 |
| TOTAL | | 20514 |

Towards the end of this course of therapy, Patient B had no evidence of systemic disease and a biopsy of the left breast only showed intraductal carcinoma with the aggressiveness and marked anaplasia having reverted back to almost normal ductal patterns, and there was very little evidence of invasion. Electron microscopy showed that the cells were certainly undergoing cell death and that Patient B was benefitting from her therapy. Atomic absorption studies were performed on some of the tumor tissue and tested for platinum; they showed that Patient B's tumor tissue had four times the platinum concentration as that of a control.

Patients C and D have also been treated for infiltrating ductal carcinoma with the platinum-transferrin complex. Both these patients have improved as a result of this therapy.

Properties of platinum-transferrin as an anti-neoplastic agent can be put in proper perspective by comparing its properties with those of a theoretically excellent clinical agent for treating malignancies. Such an agent should specifically attack and kill rapidly multiplying cancer cells and not damage normal cells. The agent should not be destroyed by the body's defense mechanism against foreign substances, because such destruction greatly reduces the length of time the anti-neoplastic agent acts effectively to eradicate cancer cells. Traumatic side effects to non-malignant cells are minimal, and the dose of the agent necessary to effect eradication of the malignant cells should be minimal. In addition, administration of the drug should cause only minor discomfort to the patient.

It has been found that the platinum-transferrin composition of the present invention achieves many of the objectives of a theoretically excellent clinical treatment for malignancy. Even though platinum-transferrin will kill rapidly growing human HeLa cells (FIG. 2), it apparently has little effect on slower growing normal human cells (FIG. 3). It has also been found in work with tumor bearing rats and human breast tissue samples that iron specifically carried by transferring accumulated in larger quantities in tissue containing malignent cells that in surrounding normal tissue. F. Warner, F. Stjernholm and I. Cohn, Medical Physics, 5: 100 (1978); M. Dodd and J. Silcock, British Journal of Cancer, 34: 556 (1976). From this work it is clear that platinum-transferrin specifically attacks cancer cells while having little or no damaging effect on slower growing normal cells. This selectivity appears to be due to the fact that malignant cells have transferrin receptors, and that they have a greater need for transferrin bound iron to support rapid cell division.

One of the most important attributes of platinum-transferrin as an anti-neoplastic agent is its ability to escape detection and destruction by the human body's immune defense mechanisms against unnatural substances. Since the cell killing agent, platinum, is bound to and hidden in a naturally occurring protein, transferrin, which the body recognizes as being normal, the platinum transferrin has not stimulated immune reactions. By not inducing immune reactions, platinum-transferrin remains in the body and provided longer term, anti-neoplastic activity. The anti-cancer agents presently in clinical use are generally destroyed by the body's defense mechanism within a few days after being administered, so the platinum-transferrin represents a significant advance in the treatment of breast carcinoma.

Only approximately 10% of the administered dose of the previously used platinum based anti-cancer agent cis-dichlorodiammine platinum (II) finally reaches the malignant breast tumor cells while the remaining 90% is stored in other tissue, excreted through the kidneys, and otherwise eliminated from the body. The cis-dichlorodiammine platinum (II) alone is thereby rendered largely ineffective in curing cancer. S. Banister, et al, Clinical Chemistry, 23: 2258 (1977); W. Wolf, et al., J. Clinical Hematology & Oncology, 7: 79(1977). Because transferrin with its attached metal is not known to be excreted from the body and should be more specifically directed to rapidly multiplying breast cells, a smaller quantity of platinum, as platinum-transferrin, can be administered to the patient to effect remission. It also appears that the platinum-transferrin can be administered by injection, thereby avoiding the discomforting intravenous drip technique generally used in the treatment of breast cancer patients.

The therapeutic dosage of platinum-transferrin has generally been found to be a dosage equivalent to 10% of the normal transferrin in the body of a patient to whom the platinum-transferrin is being administered. For example in a 70 kilogram man, it is generally found that there are 12 grams of normal human transferrin. Such a patient will be given 10% of the 12 grams as a useful therapeutic dosage, or 1.2 grams of platinum-transferrin.

The therapeutic dosage of platinum compounds not bound to transferrin is usually two to three mg per kilogram of body weight, in contrast to the approximately 0.8–3.0 mg of platinum per person necessary with the cis-platinum-transferrin complex. The remarkably lower dosage of cis-platinum-transferrin is made possible because of the breast tumor specific activity of platinum-transferrin.

Immunodiffusion assays have been performed to determine if the subjects receiving the monomeric platinum-transferrin complex were developing antibodies in their blood to platinum bound human transferrin. These tests were performed on an agar plate stained with commassee blue. A schematic drawing of the plate appears immediately below. Blood serum samples were obtained from Patients A, D, and E. These blood serum samples were placed on the agar plate in the following fashion:

0: Platinum bound human transferrin 100 ug/ml.
1: Rabbit anti-human transferrin, 100 ul.
2: Subject A, 40 ul.
3: Subject D, 40 ul.
4: Rabbit anti-human transferrin, 100 ul.
5: Subject E, 40 ul.
6: Control human serum, 40 ul.

The plate was placed in a humidified 37° C. incubator for development of precipitation. The plates were allowed to develop for about one day, after which time precipitates were observed around drops 1 and 4, the rabbit, anti-human transferrin. The precipitates indicated that drops 1 and 4 contained antibodies to the platinum bound human transferrin in drop 0. The absence of precipitates between drop 0 and drops numbered 2, 3, 5 and 6 indicated that subjects A, D and E had not developed serum antibodies to the platinum human transferrin. These blood samples were taken from Patients A, D and E three to five months after they had first received the platinum transferrin injections.

The results of these immunodiffusion assays demonstrate that subjects receiving the platinum bound human transferrin do not develop antibodies to platinum transferrin. Theoretically, this appears to be possible since transferrin is a naturally occurring blood protein which the body does not recognize as an alien substance. The transferrin probably cloaks the platinum in such a manner that it escapes detection and destruction by the body's immune system. The results of this immunological test are borne out in a clinical setting wherein the primary symptom experienced by patients receiving platinum bound human transferrin is a slight fever of one or two degrees.

The breast tumor specific properties of transferrin appear to make it ideal for combination with any toxic metal, but most research to date has focused on binding transferrin to the poisonous metal platinum. It is known from iron metabolism studies that transferrin has two receptors, which in the normal human body, bind iron ligands to the transferrin for distribution of iron in the human body. Transferrin, with a molecular weight of about 77,000 is structured as a single polypeptide chain which contains terminal sialic acid groups on two identical heterosaccharide chains, each linked to an asparagine molecule. The two metal binding sites can bind a diverse group of bivalent and trivalent metals, but Fe (III) is bound most tightly so that usually it displaces other metals. Other metals which may be bound to the transferrin receptors include Cr (III), Cu (II), Mn (II), Co (II), Cd (II), Zn (II), Ni (II), Sc, V, Ga, Pt, and the elements of the lanthanide series. Biochemistry of Nonheme Iron, Plenum Press (1980) pp. 145–146. Ruthenium is also known to bind to transferrin and is a toxic metal useful in causing regression of breast tumor cells when bound to transferrin. Gallsium is another toxic metal that should be therapeutically useful.

In accordance with preferred embodiments of the present invention, each of the two iron ligands are replaced with platinum thereby producing a platinum atom to transferrin molecule ratio of approximately 2 to 1. In order to achieve optimal therapeutic activity, the ratio of cis-platinum to iron should be approximately 1.8–2.2 atoms of platinum per molecule of transferrin. The following example illustrates a method which may be used to prepare platinum-transferrin having optimal therapeutic properties.

EXAMPLE I

A bottle having a 15 ml capacity with a screw cap is used as a reaction vessel. A 450 mg portion of pure human transferrin (essentially Fe-free) which can be obtained from Sigma Chemical Company, P.O. Box 14508, St. Louis, Mo. 63178 as Product No. T-2252, is dissolved in 10 ml 0.01M citric acid. To this mixture is added 12 mg cystine di-hydrochloride in 1 ml 0.1N HCl. After mixing, 3 mg cis-dichloro-diammine platinum (II) powder, which can be obtained from Sigma Chemical Company, P.O. Box 14508, St. Louis, Mo. 63178, is added, followed by 200 mg of sodium bicarbonate powder. The bottle is capped tightly, and left in a refrigerator at +5° C. for 45 minutes to cool the reaction mixture. The solution is transferred to a collodium bag concentrator and dialyzed under negative pressure against 100 ml phosphate buffered saline until the platinum bound transferrin solution is reduced to 5 ml (time 3–5 hours). If a white powder appears (excess cystine) it is removed by centrifugation at 10,000×G for 5 minutes. A dimeric and monomeric platinum transferrin remain in solution. The remaining clear protein solution is then applied on a Sephadex G-200 column for molecular sieving using phosphate buffered saline. A monomeric transferrin containing platinum is recovered between 250 to 300 ml of eluant. This portion is concentrated in an Aminco Concentrator until the protein concentration has reached 35–45 mg per ml. After sterilization with a Millex filter the product is kept in a refrigerator at +5° C. until used. This product contains 1.8–2.2 atoms of platinum per molecule of transferrin.

As this example demonstrates, the platinum-transferrin must be carefully prepared to avoid polymerization of the product since the polymeric form of platinum transferrin has been found to be ineffective in treating breast tumor cells. The product of the process described in Example I achieves both of these goals and results in a product that for the first time is dramatically therapeutically useful. Preparation of the product at a reduced temperature (e.g., 0°–5° C.) often avoids polymerization of the product.

It is not known if the entire cis-dichlorodiammine platinum (II) molecule is incorporated into the transferrin or if only the platinum molecule itself is bound to the transferrin. Accordingly, the product is referred to only as platinum-transferrin.

EXAMPLE II 1000 mg human transferrin obtained from Sigma Chemical Company under product No. 2252, is dissolved in 10 ml of 0.01M citric acid, using a vessel provided with a screwcap. To this solution is added 12 mg cystine dissolved in 1 ml 0.01N HCl. The cystine is added in excess to chemically "protect" the sulfhydro groups on the transferrin and prevent them from participating in any subsequent reactions. The mixture is chilled in ice water until the temperature is 0°–5° C. since it has been found that the monomeric form of platinum transferrin forms more readily at reduced temperatures. Ten mg of cis-dichloro-diammine-platinum II (cis-platinum) powder obtained from Sigma Chemical Company and identified as Sigma Product No. P-4394 is added followed by 400 mg sodium bicarbonate. The bicarbonate anion appears to initiate bonding of the platinum to transferrin. The vessel is capped and gently swirled in the ice water until the cis-platinum powder is completely dissolved. The screw cap is removed and the solution is placed in a dialysis tubing with MW cutoff of 12,000 obtained from Scientific Products and dialyzed against 500 ml phosphate buffered saline for 12 hrs. to remove the citrate and bicarbonate ions.

The dialyzate is discarded and the content of the dialysis tubing is then applied on a K-25/100 cm column (Pharmacia) packed with a slurry of Sephadex G-200 (Pharmacia) for molecular sieving. The platinum-transferrin is eluted with phosphate buffered saline. A dimeric form of the platinum transferrin is eluted between 180–230 ml. The dimeric form is discarded because it is an artifact of procedure. The monomeric form of platinum-transferrin is eluted from the column between 250–330 ml. This solution is concentrated to 10 ml (which is about 50 mg/ml) using an Aminco concentrator, Model 52 (Amicon) provided with a Diaflo membrane, UM-5 (Amicon) operating under a pressure of 40 psi of nitrogen.

The final platinum-transferrin product is sterilized by passing through a Millex SLGS-025-OS.22 u filter (Millipore) to remove bacteria or other particulate matter which may be present, and the platinum-transferrin is stored in sterile plastic tubes (Falcon) at +5° C. until used.

The transferrin which is used as a starting material can be obtained in essentially iron free form (99% pure) from Sigma Chemical Company. However, if the transferrin is not essentially iron free, it can be treated with a 0.1M phosphate buffer ($KH_2PO_4$) adjusted with KOH to a pH of 5.0. A chelating agent such as ethylene diamine tetraacetate is then added to take free iron out of solution. An essentially iron free starting material remains. When the iron is removed from the transferrin, the red solution becomes colorless.

I claim:

1. Monomeric platinum transferrin prepared by reacting cis-diamminedichloroplatinum II with essentially iron free human transferrin in the presence of cystine at 0°–5° C., then separating monomeric platinum transferrin from polymeric platinum transferrin.

2. Platinum transferrin of claim 1, wherein [platinum] *transferrin* is reacted with cis-diamminedichloroplatinum II in the presence of bicarbonate anion.

*3. A method for preparing monomeric platinum transferrin comprising:*

*reacting cis-diamminedichloroplatinum II with essentially iron-free human transferrin in the presence of cystine at 0°–5° C; and*

*separating monomeric platinum transferrin from polymeric platinum transferrin.*

*4. The method of claim 3, wherein the transferrin is reacted with cis-diamminedichloroplatinum II in the presence of bicarbonate anion.*

*5. A process for preparing a complex of serum transferrin and the cis isomer of diamminedichloroplatinum (II) comprising preparing an aqueous solution of serum transferrin and adding thereto a sufficient quantity of the cis isomer of diamminedichloroplatinum (II) to bring the final ratio of said cis isomer of diamminedichloroplatinum (II) to said serum transferrin to approximately a 2:1 molar ratio.*

* * * * *